US005593384A

United States Patent [19]

Halem

[11] Patent Number: 5,593,384

[45] Date of Patent: Jan. 14, 1997

[54] CONTROLLED INFUSION ADMINISTRATION OF PHARMACEUTICALS

[76] Inventor: Stephen H. Halem, 47 Sargent St., Newton, Mass. 02158

[21] Appl. No.: 327,824

[22] Filed: Mar. 23, 1989

[51] Int. Cl.$^6$ .................... A61M 31/00

[52] U.S. Cl. .................... 604/54; 604/57; 604/93; 604/104; 424/438

[58] Field of Search .................... 424/436, 438; 604/104–109, 93, 54, 57, 271, 891.1 (U.S. only), 891.2 (U.S. only)

[56] References Cited

U.S. PATENT DOCUMENTS

| | | | |
|---|---|---|---|
| 4,202,329 | 5/1980 | Kortum | 128/303 R |
| 4,308,859 | 1/1982 | Child | 604/54 |
| 4,346,714 | 8/1982 | Child | 604/54 |
| 4,365,632 | 12/1982 | Kortum | 119/14.02 |
| 4,690,825 | 9/1987 | Won | 424/501 |
| 4,731,054 | 3/1988 | Billeter et al. | 604/57 |

FOREIGN PATENT DOCUMENTS 8800817 of 0000 WIPO .

*Primary Examiner*—Randy C. Shay
*Attorney, Agent, or Firm*—Fish & Richardson P.C.

[57] ABSTRACT

A method for administering a pharmaceutical to an animal includes imbibing a plurality of carriers with the pharmaceutical, placing a barrier into the animal, defining a first zone and a second zone within the animal, the barrier permitting passage of the pharmaceutical between the zones and impeding passage of the carriers between the zones, and placing the imbibed carriers into the first zone. Also, a method for treating mastitis in a mammal includes imbibing a plurality of carriers with an antibiotic effective in combating a mastitis-causing pathogen, placing a barrier into the udder of the mammal, defining a first zone and a second zone within the udder, the barrier permitting passage of the pharmaceutical and impeding passage of the carriers, and placing the imbibed carriers into the first zone. Also, apparatus for administering a pharmaceutical to an animal includes a barrier adapted to permit passage of the pharmaceutical and to resist passage of carriers adapted to reversibly hold the pharmaceutical, the barrier being positionable within the animal such that the barrier may define a first zone and a second zone within the animal, and a plurality of such carriers positionable within the first zone, whereby as the pharmaceutical is released from the carriers it may pass the barrier from the first zone into the second zone.

35 Claims, 4 Drawing Sheets

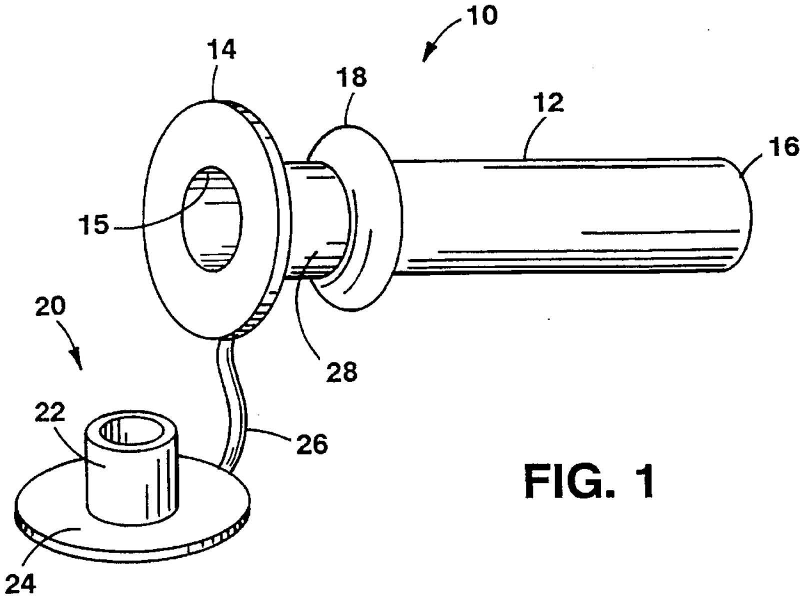
FIG. 1
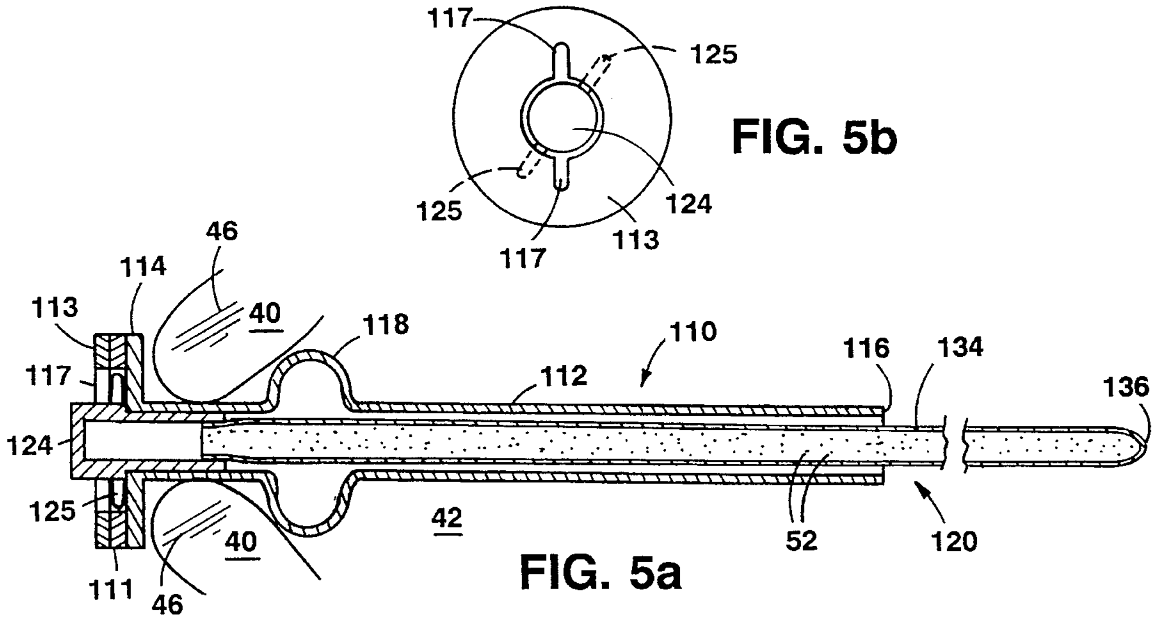
FIG. 5b
FIG. 5a

CONTROLLED INFUSION ADMINISTRATION OF PHARMACEUTICALS

BACKGROUND OF THE INVENTION

This invention relates to controlled release administration of pharmaceuticals.

It is desirable in the treatment of certain diseases of veterinary and/or human medical interest, such as, for example, certain infections or tumors, to be able to deliver a pharmaceutical agent to a particular site in the body of the animal or person suffering from the disease and to provide for such local delivery at levels at least high enough to provide an effective dose over a sustained period of time.

Mastitis is one such disease. Mastitis is an infection of the breast or udder of a mammal, usually caused by a bacterial invasion. Mastitis in dairy animals can cause poor milk quality, a reduction in milk production, or even loss of the animal.

Relief from an infection can be provided, for example, by administering an antibiotic to the animal. Administration of the antibiotic by a single injection at the site of the infection can result in a high initial level of the pharmaceutical agent followed by a rapid decline in level to a level eventually of very little pharmaceutical agent, even where, as may be the practice, the antibiotic is suspended in an ointment base intended to provide a s low release of the antibiotic at the site in the body.

Conventionally, the antibiotic can be kept above a level that provides an effective dose by administering an initial loading dose followed by repeated maintenance doses. Thus, using conventional means of administration, maintaining a dose sufficient to combat an infection successfully or to provide prophylaxis against recurrent infection can require repeated injection and can result in problems of pharmaceutical overdose. At excessively high levels, an antibiotic can irritate the tissues at the site of administration, and can impede the phagocytic activities of the leucocytes, which normally help to remove invading bacteria from the infection site.

In the case, for example, of bovine mastitis the antibiotic conventionally is administered by infusion or injection of a quantity of antibiotic directly into the udder. Following such conventional administration, the antibiotic can persist in the udder and can appear in the milk at levels unacceptable for human consumption for some time beyond the time required for clearing the infection. At levels lower than an effective dose, which can nevertheless result in unacceptable levels in the milk, the antibiotic fails to produce the desired therapeutic effect.

SUMMARY OF THE INVENTION

In general, in one aspect, the invention features a method for administering a pharmaceutical to an animal, including imbibing a plurality of carriers with the pharmaceutical, placing a barrier into the animal, so that the barrier defines a first zone and a second zone within the animal, the barrier permitting passage of the pharmaceutical between the zones and impeding passage of said carriers between the zones, and placing the imbibed carriers into the first zone.

In preferred embodiments, the step of placing the imbibed carriers includes injecting them into the first zone, or directing them through a body passage of the animal; the step of placing the imbibed carriers into the first zone includes directing them through a conduit, such as a cannula or a trochar, which preferably is placed in a body passage of the animal; the imbibed carriers are directed through the body passage or through the conduit, cannula, or trochar by infusing them or injecting them; the conduit is left in place in the body passage for a time after the imbibed carriers are directed through the conduit.

In another aspect, the invention features a method for administering a pharmaceutical to an animal including providing a plurality of carriers adapted to reversibly hold the pharmaceutical, enclosing the carriers within a space defined by a barrier that is adapted to permit passage of the pharmaceutical and to impede passage of the carriers, and placing the barrier enclosing the carriers at a site within the animal, so that as the pharmaceutical is released from the carriers it may pass the barrier to the site from the defined space.

In preferred embodiments, the carriers are imbibed with the pharmaceutical before they are enclosed within the defined space, after they are enclosed within the defined space, after the barrier enclosing the carriers is placed at a site within the animal, or at more than one time interval.

The method of the invention makes it possible to maintain a high concentration of medication at a local area in the animal while achieving low overall doses. The porous polymeric beads allow for a controlled release of the medication into the immediate environment surrounding the membrane. At any time during the course of the treatment, the barrier and the carriers retained by it can be removed from the site, thus removing the source of the pharmaceutical agent. As a result, the period of time during which residual pharmaceutical agent persists in the animal can be substantially shortened.

In another aspect the invention features a method for treating mastitis in a mammal, including imbibing a plurality of carriers with an antibiotic effective in combating a mastitis-causing infection, placing a barrier into the udder of the mammal, the barrier defining a first zone and a second zone within the udder, the barrier being permeable to the pharmaceutical and impermeable to the carriers, and placing the imbibed carriers into the first zone.

In preferred embodiments the first zone includes a portion of a lower gland cistern of the udder and is accessible from outside the udder by way of a lactiferous duct, preferably by way of a conduit traversing a lactiferous duct; the conduit can be reversibly closed; the carriers include porous polymeric beads; and the antibiotic includes tetracycline.

The method of the invention for treating mastitis provides for the local and controlled release of the selected antibiotic at the point of infection. Administration of antibiotic by the method of the invention permits both treatment of active mastitis and prophylactic prevention of the development of mastitis. The method can be employed with either a lactating cow which has mastitis or as prophylactic therapy for the drying-off cow and for the cow that is about to freshen back into lactation.

In another aspect, the invention features a method for treating mastitis in a mammal, including placing into a mamma of the mammal a plurality of carriers that are adapted to reversibly hold an antibiotic, and that are imbibed with an antibiotic effective in combating a mastitis-causing pathogen. In preferred embodiments the carriers are injected into the mamma.

In another aspect the invention features a method for treating mastitis in a mammal, including imbibing a plurality of carriers with an antibiotic effective in combating a mastitis-causing pathogen, placing a barrier into the udder of the mammal, so that the barrier, which permits passage of the pharmaceutical between the zones and impedes passage of the carriers between the zones, defines a first zone and a second zone within the udder, and placing the imbibed carriers into the first zone.

In another aspect the invention features apparatus for administering a pharmaceutical to an animal, including a plurality of carriers adapted to reversibly hold the pharmaceutical, and a barrier adapted to permit passage of the pharmaceutical and to prevent passage of the carriers and positionable at a site within the animal, whereby as the pharmaceutical is released from the carriers it may pass the barrier from the first zone into the second zone.

In another aspect the invention features apparatus for administering a pharmaceutical to an animal, including a barrier adapted to permit passage of the pharmaceutical and to prevent passage of the carriers and positionable at a site within the animal such that the barrier defines a first zone and a second zone within the animal, and a plurality of carriers adapted to reversibly hold the pharmaceutical positionable within the first zone, whereby as the pharmaceutical is released from the carriers it may pass the barrier from the first zone into the second zone.

In another aspect, the invention features apparatus for administering a pharmaceutical to an animal, including a plurality of carriers adapted to reversibly hold the pharmaceutical, a barrier adapted to permit passage of the pharmaceutical and to resist passage of the carriers, the barrier being positionable within the animal such that the barrier may define a first zone and a second zone within the animal, and a channel for passing the carriers holding the pharmaceutical into the first zone, whereby as the pharmaceutical is released from the carriers it may pass the barrier from the first zone into the second zone.

In preferred embodiments, the carriers comprise porous polymeric beads; the porous polymeric beads are of styrene divinylbenzene; the porous polymeric beads are at least 5 microns in diameter, preferably at least 10 microns in diameter; the porous polymeric beads have a network of pores in which the pharmaceutical can be reversibly held; the barrier includes a porous membrane or a mesh; the barrier includes a polyvinylidine difluoride membrane; the dimensions of the pores or of the mesh are selected so that the carriers are restricted in passing through the barrier; the barrier has the shape of an envelope, a pad, a pillow, a barbell, or a tube closed at one end; the means for placing the barrier into the animal includes a conduit adapted to traverse a body passage of the animal; the apparatus further includes means for infusing the imbibed carriers through the conduit into the first zone; at least a portion of a margin of the barrier is affixed to the conduit; the apparatus further comprises means for infusing the imbibed carriers through the conduit, so that infusing the imbibed carriers effects placing the barrier; the conduit comprises a cannula or a trochar; the conduit is provided with a retainer adapted for resisting removal of the conduit from the passage, and is provided with a retainer adapted for preventing the conduit being drawn into the animal, or both.

In preferred embodiments the first zone includes a portion of a gland cistern of the udder, and the step of placing the imbibed carriers into the first zone includes directing the imbibed carriers through a lactiferous duct; the step of placing the imbibed carriers into the first zone includes directing them through a conduit, such as a cannula or a trochar, which preferably is placed in a lactiferous duct; the step of directing the imbibed carriers through the lactiferous duct or through the conduit, cannula or trochar includes infusing or injecting them; the conduit is left in place in the lactiferous duct; and the conduit is reversibly closed after the imbibed carriers are directed through it.

The method of the invention for treating mastitis can be carried out by the farmer without requiring complicated veterinary training or apparatus. The device of the invention for treating mastitis is straightforward, simple, and easy to use, and does not present an unfamiliar appearance to the user. Handling and using the device requires manipulations little different from those employed by the farmer or veterinarian in the course of routine treatments for diseases and disorders of the udder. The device is inexpensive to manufacture. The device can be packed in an aseptically sealed foil package, in which it is kept moist so that the membrane sac is kept soft and the entire apparatus is kept sterile.

DESCRIPTION OF THE PREFERRED EMBODIMENTS

Other features, objects and advantages of the invention will become apparent from the following detailed description when read in connection with the accompanying drawings, in which:

FIG. 1 is a perspective view of an insertion device according to the invention;

Figures 2, 2A, 2B:
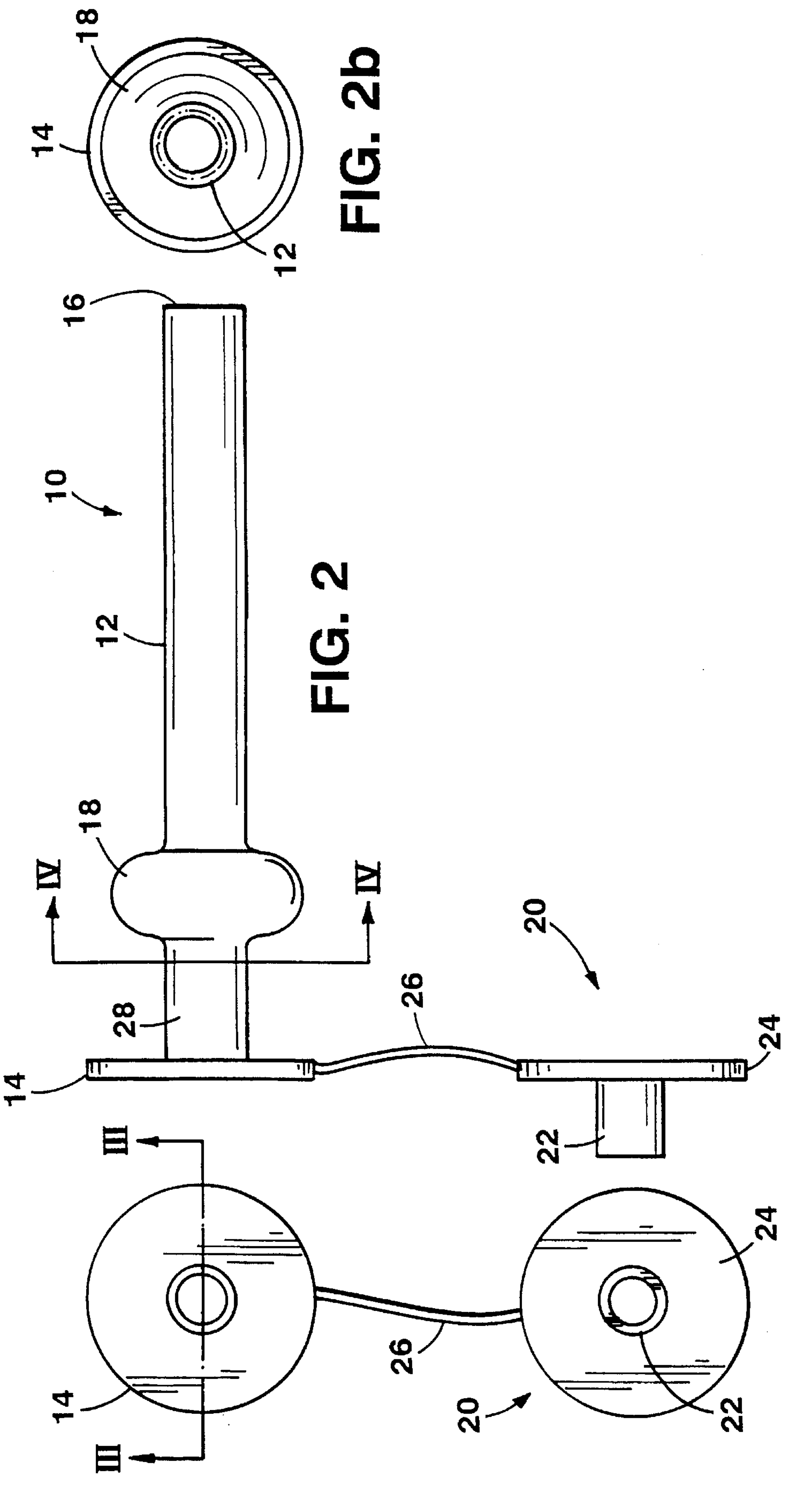
FIG. 2 is an elevational view of the insertion device of FIG. 1.
Figure 3:
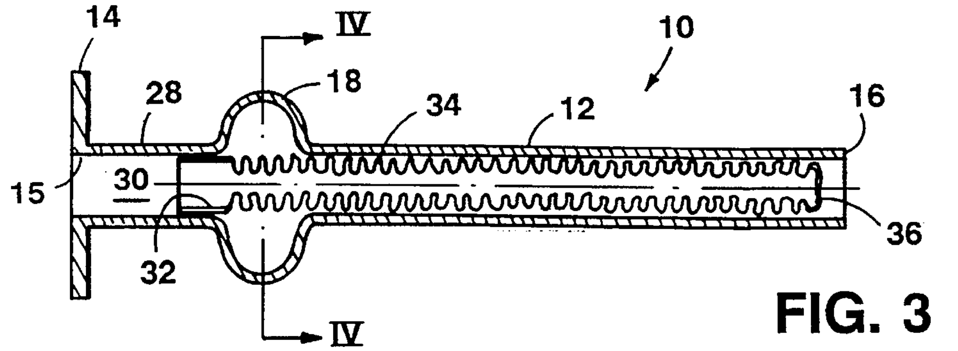
Figure 4:
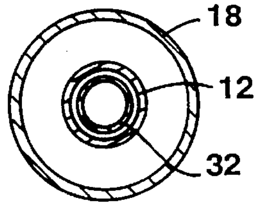
Figure 3A:
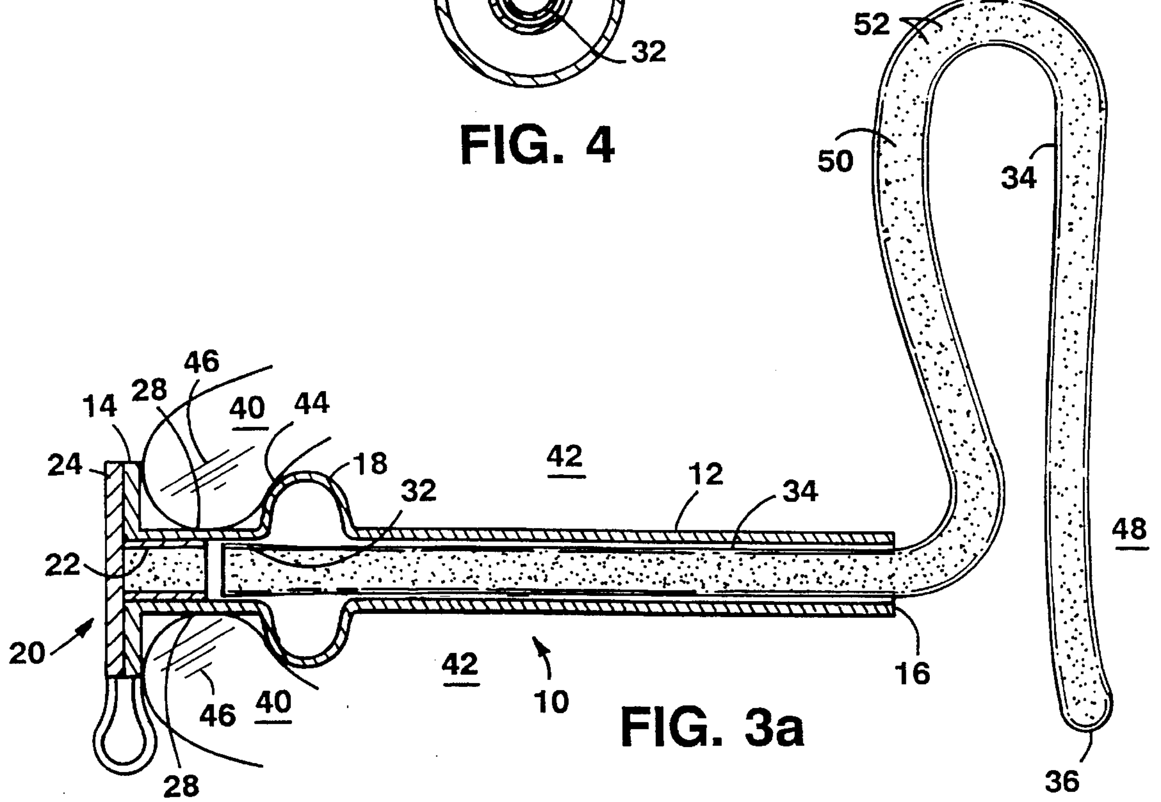

FIG. 2*a* is a view from the distal end of the insertion device of FIG. 2;

FIG. 2*b* is a view from the proximal end of the insertion device of FIG. 2;

FIG. 3 is a sectional view through the long axis of the insertion device of FIG. 2 at III—III, showing the device ready for emplacement of the membrane sac in the animal;

FIG. 3*a* is a sectional view of the device as in FIG. 3 showing the membrane sac fully inflated into the lower cistern of an udder of an animal and showing the membrane sac full of porous polymeric beads imbibed with an antibiotic;

FIG. 4 is a sectional view thru IV—IV of the barrel of the apparatus shown in FIG. 3;

FIG. 5*a* is a sectional view through the long axis of an alternative insertion device according to the invention, showing a trochar inserted into the teat and showing a membrane sac prefilled with porous polymeric beads imbibed with an antibiotic; and FIG. 5*b* is a view from the distal end of the insertion device of FIG. 5*a*, showing interlock of the end cap with the trochar hub when the membrane sac has been fully inserted.

In the following example, which is provided for illustrative purposes and is not intended to limit the claims, a device according to the invention is described which is suitable, for example, for administering carriers imbibed with an antibiotic into an udder of a bovine mammal for treatment of mastitis.

With reference now to FIG. 1, an insertion device of the invention includes a trochar, shown generally at 10, and an end cap, shown generally at 20. The trochar includes barrel 12 and hub 14 attached at a distal end of barrel 12. Hub 14 has a hole 15 aligned with the lumen of barrel 12. The edge of the barrel wall at a proximal end 16 of barrel 12 is rounded so that it slides easily through the lactiferous duct during insertion without irritating the tissues of the teat. The wall of barrel 12 is expanded radially at a suitable distance proximal from hub 14 to form a retainer 18 whose function will be described below with reference to FIG. 3*a*. Cap 20 comprises flange 22 and cover 24. Cap 20 can conveniently be attached to trochar 10 by means of strap 26 running from cover 24 of cap 20 to hub 14 of trochar 10.

With reference now to FIGS. 2, 2*a* and 2*b*, the insertion device of FIG. 1 is shown in elevation, distal end, and proximal end views respectively. Trochar 10 resembles a teat cannula, adapted for insertion into the udder of the animal by way of a lactiferous duct in a teat. Barrel 12 of trochar 10 is a hollow tube about 4.5 mm in outside diameter and about 3.8–4.0 mm in inside diameter, and about 45 mm in length. The length of the trochar is sufficiently great so that when trochar 10 is in place, the proximal end of the barrel reaches well into the teat cistern. The inside diameter is sufficiently large that the membrane sac can be fully stored within it, as described below with reference to FIGS. 3 and 3*a*. The wall of the trochar barrel is sufficiently thick that trochar 10 will not collapse while in place. The outside diameter of trochar 10 is not so large as to overstress the teat sphincters or the inner tissues of the teat. The outside diameter of flange 22 of cap 20 is selected to approximate the diameter of hole 15 in hub 14 so that flange 22 of cap 20 can be press fitted into hole 15, providing a seal at the distal end of trochar 10.

FIG. 3 is a sectional view through the long axis of trochar 10, showing a membrane sac 34 contained within barrel 12 and ready for insertion into the animal. Membrane sac 34 is a generally tubular sac of a porous material, closed at a proximal end 36, and open at a distal end 32, defining a margin. Distal end 32 of membrane sac 34 is affixed to the inner surface of barrel 12 by welding, and membrane sac 34 is gathered, pleated or folded so that it is entirely contained within barrel 12.

Porous membrane sac 34 is a selectively permeable barrier having a porosity, or mesh dimensions, selected to permit passage through the membrane of the pharmaceutical agent to be used, and to prevent the passage through the membrane of the porous polymeric beads in which the pharmaceutical agent is to be carried, and may be characterized as a semipermeable membrane barrier. Porous polymeric beads are available, for example, from Advanced Polymer Systems, Inc., Redwood City, Calif. A pore size or mesh size of not greater than 5 micrometers is suitable for use with porous polymeric beads having nominal diameters of 35 micrometers. Preferably porous membrane sac 34 is made of a porous polymeric material, which is soft and supple when moist, and which is biocompatible. Suitable materials include, for example, polyvinylidine difluoride membranes; such materials are available, for example, as Durapore® membranes, having a range of pore sizes, from Millipore, Inc.

Porous membrane sac 34 preferably is about 4 mm in diameter and sufficiently long so that, when fully expanded as shown in FIG. 3*a*, it extends to a length of about 15 cm within the lower gland cistern of the udder.

FIG. 3*a* is a sectional view showing the device in use. Trochar 10 passes through a lactiferous duct within teat cistern 42 of the teat 40, and porous membrane sac 34 has been filled with porous polymeric beads, for example 52, so that it is fully expanded within lower gland cistern 48 of the udder. Teat sphincter 46 closes the lactiferous duct about the portion 28 of barrel 12 of trochar 10 situated between hub 14 and retainer 18, providing a seal between the teat and the trochar. Hub 14 prevents barrel 12 being drawn into and lost within the udder. Retainer 18 aids in retaining barrel 12 and membrane sac 34 within the teat and the udder by resting against the inner wall of the teat at points 44 adjacent teat sphincter 46. Cap 20 is fitted within the distal end of trochar 10, closing trochar 10 to prevent outflow through barrel 12 of any of the contents of teat cistern 42 or gland cistern 48. With the device thus emplaced and the membrane sac thus expanded, the membrane provides a barrier that defines a first zone 50 contained within the lumen of membrane sac 34, and a second zone 48 within the lower gland cistern of the udder. Fluids, and dissolved or suspended matter whose dimensions are small enough to pass through the pores of the membrane, can pass between zone 50 and zone 48, while suspended matter too large to pass through the pores of the membrane are retained within the zone in which they are located once membrane sac 34 is filled.

Thus, for example, porous polymeric beads having dimensions too large to permit their passage through the pores of the membrane can be imbibed with a pharmaceutical agent, and the membrane sac can be expanded by filling it with the imbibed porous polymeric beads. The pharmaceutical agent then gradually passes out from the porous polymeric beads into lumenal space 50 within membrane sac 34, and then passes through the pores of membrane sac 34 into lower gland cistern 48 of the udder, where it works its therapeutic effect. The rate of flow of the pharmaceutical agent into lower gland cistern 48 depends generally upon its rate of movement out from the porous polymeric beads, which is in turn dependent upon the properties of the porous polymeric beads themselves, as described below, and in part upon diffusion rates of the pharmaceutical agent within lumenal space 50 of expanded membrane sac 34 and within lower gland cistern 48 itself.

The porous polymeric beads are imbibed with the desired pharmaceutical agent generally as described below, and the imbibed porous polymeric beads are held in a suspension suitable for delivery, such as, for example, a suspension of the pharmaceutical agent in a physiological saline solution. Then the suspended imbibed porous polymeric beads are directed into the membrane sac, located within the body where delivery of the pharmaceutical agent is desired. The apparatus of the invention provides a selectively permeable barrier defining a space for retaining the porous polymeric beads within a selected locality in the body while the pharmaceutical agent moves out from the porous polymeric beads across the barrier to the site where delivery of the pharmaceutical agent is desired.

With reference now particularly to FIGS. 3, 3*a*, the device is used to practice the method of the invention as follows. Trochar 10 is provided with porous membrane sac 34, as described generally above with reference to FIGS. 3, 4, and membrane sac 34 is gathered within barrel 12 of trochar 10. Then trochar 10 is inserted, proximal end 16 foremost, by way of a lactiferous duct into the teat of the gland in which treatment is desired. As the barrel traverses the lactiferous duct, a point is reached where further inward progress may be hampered by retainer 18. Massaging the teat aids in relaxing the teat sphincter sufficiently to permit the retainer to pass inwardly beyond the sphincter. Once retainer 18 has passed beyond teat sphincter 46 and into teat cistern 42 of the teat, insertion of trochar 10 is complete. Further movement of trochar 10 into the udder is inhibited by hub 14, which now rests against the outer surface of the teat adjacent teat sphincter 46, and movement of trochar 10 out from the teat is hampered by retainer 18, which rests against the inner surface of the teat at points 44 adjacent teat sphincter 46.

Once trochar 10 has been inserted, porous membrane sac 34 is filled and expanded by introducing a suspension of porous polymeric beads 52 into the lumenal space defined by membrane sac 34 by way of hole 15 in hub 14 and lumen 30 of trochar barrel 12. The open distal end 32 of membrane sac 34, affixed to trochar barrel 12 as described above with reference to FIG. 3, defines a margin about an opening in the barrier through which the carriers can be directed into the lumenal space of the membrane sac. The suspension of porous polymeric beads can be introduced under low pressure, for example, by means of a syringe. Once membrane sac 34 has been fully expanded, as shown for example in FIG. 3*a*, end cap 20 is fitted firmly into hole 15 in hub 14 to close the distal end of trochar 10.

The pharmaceutical agent moves gradually out from porous polymeric beads 52 into the space 50 within the lumen of the filled membrane sac 34, and passes membrane sac 34 into the cistern of the udder. When the pharmaceutical agent has substantially dissipated, the entire apparatus is removed. For further administration, the device can be replaced in the teat, or, alternatively, a new device can be placed in the teat, and filled again with imbibed porous polymeric beads as described above. Alternatively, the depleted porous polymeric beads can be withdrawn or drained out from the membrane sac, whereupon the membrane sac collapses and is ready to be filled again with imbibed porous polymeric beads.

Figure 5:
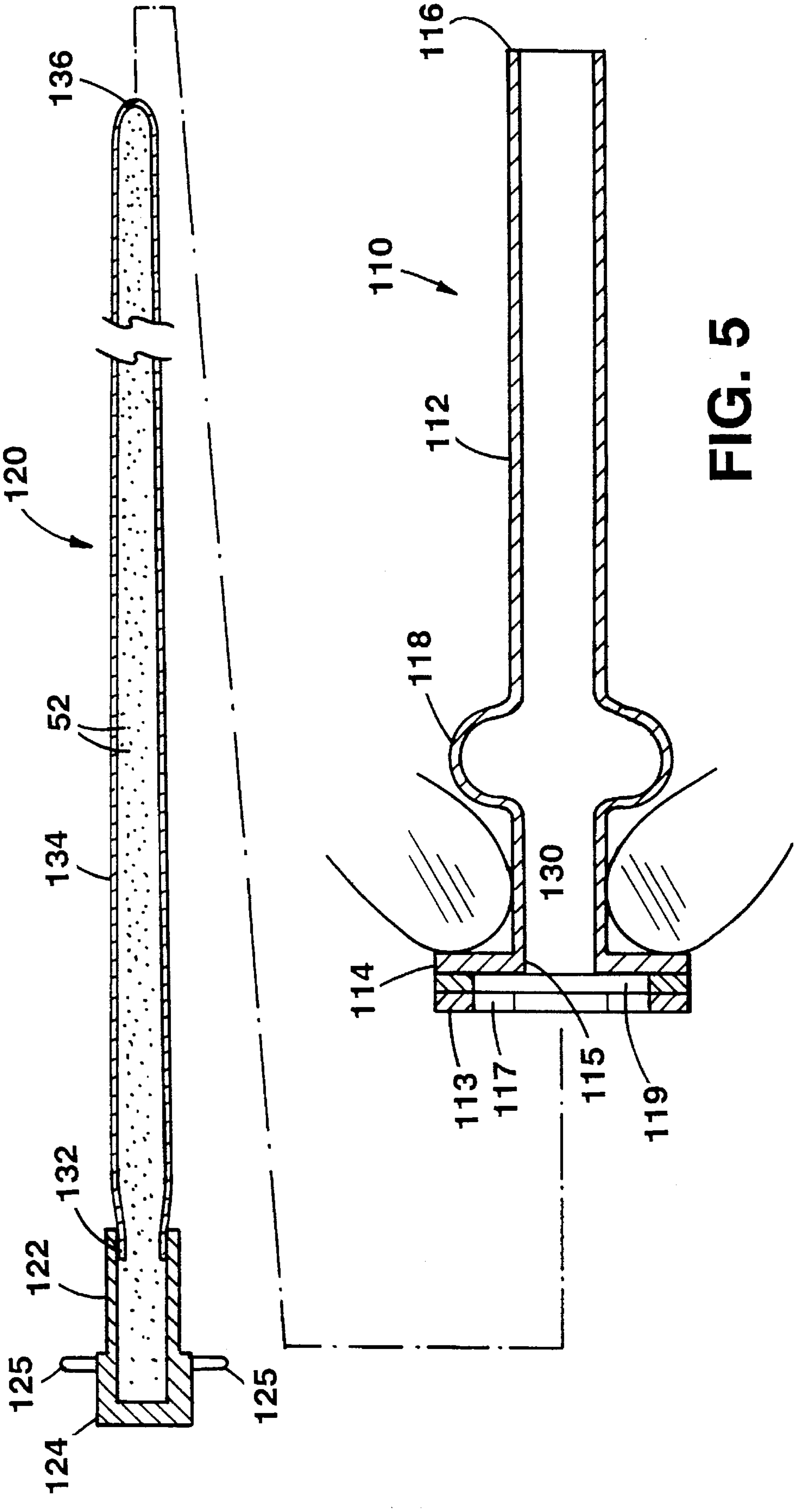

In alternative embodiments, the barrier is filled with porous polymeric beads before it is placed into the animal. FIGS. 5, 5*a* and 5*b* show an example of such an embodiment, suitable for administering an antibiotic into an udder of a bovine mammal for treatment of mastitis. Such an insertion device includes a trochar, shown in FIG. 5 generally at 110, inserted into the animal's teat, and a membrane sac and cap, shown in FIG. 5 generally at 120 ready for insertion through the trochar. The trochar includes barrel 112 and hub 114 attached at a distal end of barrel 112. Hub 114 has a hole 115 aligned with the lumen of barrel 112. The edge of the barrel wall at a proximal end 116 of barrel 112 is rounded so that it slides easily through the lactiferous duct during insertion without irritating the tissues of the teat. The wall of barrel 112 is expanded radially at a suitable distance proximal from trochar hub 114 to form a retainer 118 that functions as does the retainer 18 described above with reference to FIG. 3*a*. The barrel 112, trochar hub 114, hole 115, and retainer 118 are configured and dimensioned generally similarly to the respective barrel 12, hub 14, hole 15, and retainer 18 of trochar 10 as described with reference to FIGS. 2, 2*a*, and 2*b*. Referring again to FIGS. 5, 5*a* and 5*b*, the membrane sac 134 is a generally tubular sac of a porous material, closed at a proximal end 136, and affixed at a distal end 132 by welding to flange 122 of end cap 124. Membrane sac 134 is configured and dimensioned generally similarly to the membrane sac 34 as described above with reference to FIG. 3, and made from generally similar materials.

Referring now to FIGS. 5, 5*b*, slotted annular keeper 113 is affixed to trochar hub 114 by means of annular spacer 111. Distal end cap 124 is provided with radially projecting retainer pins 125. Retainer pins 125, spacer 111, and slots 117 in annular keeper 113 are configured and dimensioned so that distal end cap 124 and annular keeper 113 cooperate to retain end cap 124 in place within hole 115 when the membrane sac 134 has been fully inserted through the lumen of barrel 112 into the teat cistern 42, as described below.

Membrane sac 134, prefilled with carriers 52, is emplaced into the udder as follows. Trochar 110 is inserted, proximal end 116 foremost, by way of a lactiferous duct into the teat of the gland in which treatment is desired, and retainer 118 and trochar hub 116 cooperate with teat 40 and teat sphincter 46 generally similarly to retainer 18 and hub 16 as described above with reference to FIGS. 3 and 3*a*. Once trochar 110 has been inserted, membrane sac 134 is inserted proximal end 136 foremost by way of hole 115 in trochar hub 114 and lumen 130 of trochar barrel 112 into the gland cistern 42 of the udder. Near completion of the insertion as end cap 124 enters hole 115 in hub 114, retainer pins 125 are aligned with slots 117 on annular keeper 113 and pass through the slots into the space 119 defined between the annular keeper and the hub. Then end cap 124 is rotated about its long axis so that the pins 125 are nonaligned with slots 117, as shown for example in FIG. 5*b*, whereby the end cap is retained within the hub.

The embodiment using a prefilled membrane sac, as described for example above with reference to FIGS. 5, 5*a*, 5*b* can be simpler to use than the embodiment described with reference to FIGS. 1 through 3*a*. The prefilled membrane sac can be provided ready-to-use for example in a sterile foil pac. Its use requires no further apparatus than the trochar, and the user familiar with teat cannulization can insert the trochar without difficulty.

Other Embodiments

Other embodiments are within the following claims. For example, the trochar can be constructed of other materials, such as, for example, other polymers having suitable structural properties; or stainless steel; or some combination of materials.

Other porous polymeric beads can be used, made from other materials or having other porosities as described, for example, in U.S. Pat. No. 4,690,825, herein incorporated by reference.

Other carriers than porous polymeric beads can be used, including those used in known approaches such as, e.g., microencapsulation, lysosomal delivery, and emulsification.

Other shapes of barrier can be used, provided that the barrier defines a first zone to retain the imbibed carriers and a second zone including the site at which the pharmaceutical agent is to be delivered.

The barrier can be positioned at the site within the body of the animal to be treated by any of a variety of methods. For example, the barrier can be surgically implanted. A barrier for surgical implantation can be shaped as appropriate for the site in which it is to be placed, and the carriers can be placed within the enclosed space defined by the barrier either before the barrier is implanted or afterwards, as may be convenient. Thus a barrier for surgical implantation can be prepared in advance of implantation by, for example, placing imbibed carriers within the barrier and storing the carrier-filled barrier in a suitable suspension such as a suspension of the pharmaceutical in a physiological saline solution. Such a carrier-filled barrier can fully enclose the space defined within it, and need not have an opening for introduction or removal of carriers following implantation.

The trochar need not be left in place once the barrier has been emplaced. Where the trochar is left in place, other means can be used to preventing it from falling out. In embodiments where the barrier (as, example a membrane sac) is prefilled and is emplaced by passing it through a cannula or trochar, any of a variety of means for retaining the membrane sac within the trochar or cannula can be used.

The method can be used, with suitable adaptation of the apparatus (within the skill of the art), for treatment of any of a variety of veterinary and human medical applications. It can be used for delivery to body cavities other than the gland cistern, or to other organs than the udder; it can be used for treatment of any of a variety of local infections, such as Otitis Media and related infections of the ear, suppurative arthritis, foot rot, and the like.

Other pharmaceuticals than antibiotics can be delivered, depending upon the particular therapeutic effect desired, such as, for example, anticancer agents; antiinflammatory agents; or anaesthetic or analgesic agents.

I claim:

1. A method for administering a pharmaceutical to an animal, comprising imbibing a plurality of carriers with the pharmaceutical, placing a barrier into the animal, said barrier defining a first zone and a second zone within the animal, said barrier permitting passage of the pharmaceutical between said zones and impeding passage of said carriers between said zones, and placing said imbibed carriers into said first zone, wherein the step of placing said imbibed carriers includes injecting said imbibed carriers into said first zone.

2. The method of claim 1 wherein the step of placing said imbibed carriers into said first zone includes directing said imbibed carriers through a body passage of the animal.

3. The method of claim 2 wherein the step of directing said imbibed carriers includes infusing said imbibed carriers through said body passage.

4. The method of claim 2 wherein the step of directing said imbibed carriers includes injecting said imbibed carriers through said body passage.

5. The method of claim 1 wherein the step of placing said imbibed carriers into said first zone includes directing said imbibed carriers through a conduit.

6. The method of claim 5 and further including the step of placing said conduit in a body passage of the animal.

7. The method of claim 5 or 6 wherein the step of directing said imbibed carriers includes infusing said imbibed carriers through said conduit.

8. The method of claim 5 or 6 wherein the step of directing said imbibed carriers includes injecting said imbibed carriers through said conduit.

9. The method of claim 6 and further including permitting said conduit to remain in place in said body passage for a time following the step of directing said imbibed carriers through said conduit.

10. The method of claim 2 wherein the step of placing said imbibed carriers into said first zone includes directing said imbibed carriers through a cannula.

11. The method of claim 2 wherein the step of placing said imbibed carriers into said first zone includes directing said imbibed carriers through a trochar.

12. A method for administering a pharmaceutical to an animal, comprising providing a plurality of carriers comprising means for storing and releasing the pharmaceutical, enclosing said carriers within a space defined by a porous semipermeable membrane barrier, said barrier comprising means for permitting passage of the pharmaceutical and for impeding passage of said carriers, and placing said barrier enclosing said carriers at a site within the animal, whereby as the pharmaceutical is released from said carriers it may pass said barrier to said site from said space while said carriers remain within said space, further including the step of imbibing said carriers with the pharmaceutical subsequent to the step of enclosing said carriers within said space and further including the step of imbibing said carriers with the pharmaceutical subsequent to the step of placing said barrier enclosing said carriers at a site within the animal.

13. A method for treating mastitis in a mammal, comprising placing into a mamma of said mammal a plurality of carriers imbibed with an antibiotic effective in combating a mastitis-causing pathogen, said carriers comprising means for reversibly holding said antibiotic.

14. The method of claim 13 wherein said step of placing said imbibed carriers includes injecting said imbibed carriers into said mamma.

15. A method for treating mastitis in a mammal, comprising imbibing a plurality of carriers with an antibiotic effective in combating a mastitis-causing pathogen, placing a barrier into the udder of said mammal, said barrier defining a first zone and a second zone within said udder, said barrier permitting passage of said antibiotic between said zones and impeding passage of said carriers between said zones, and placing said imbibed carriers into said first zone.

16. The method of claim 15 wherein said first zone comprises a portion of a gland cistern of said udder, and the step of placing said imbibed carriers into said first zone includes directing said imbibed carriers through a lactiferous duct.

17. The method of claim 16 wherein the step of directing said imbibed carriers includes infusing said imbibed carriers through said lactiferous duct.

18. The method of claim 16 wherein the step of directing said imbibed carriers includes injecting said imbibed carriers through said lactiferous duct.

19. The method of claim 15 wherein the step of placing said imbibed carriers into said first zone includes directing said imbibed carriers through a conduit.

20. The method of claim 19 and further including the step of placing said conduit in a lactiferous duct.

21. The method of claim 20 and further including permitting said conduit to remain in place in said lactiferous duct for a time following the step of directing said imbibed carriers through said conduit.

22. The method of claim 20 and further including the step of reversibly closing said conduit following the step of directing said imbibed carriers through said conduit.

23. The method of claim 19 wherein the step of directing said imbibed carriers includes infusing said imbibed carriers through said conduit.

24. The method of claim 19 wherein the step of directing said imbibed carriers includes injecting said imbibed carriers through said conduit.

25. The method of claim 15 wherein the step of placing said imbibed carriers into said first zone includes directing said imbibed carriers through a cannula.

26. The method of claim 15 wherein the step of placing said imbibed carriers into said first zone includes directing said imbibed carriers through a trochar.

27. Apparatus for administering a pharmaceutical to an animal comprising, a plurality of carriers comprising means for reversibly holding the pharmaceutical, a semipermeable barrier comprising means for permitting passage of the pharmaceutical and for resisting passage of said carriers, said barrier being positionable within the animal such that said barrier may define a first zone and a second zone within the animal, and a channel for passing into said first zone said carriers holding the pharmaceutical, whereby as the pharmaceutical is released from said carriers it may pass said barrier from said first zone into said second zone while said carriers remain in said first zone, further comprising an injector for injecting said imbibed carriers through said conduit into said first zone.

28. Apparatus for administering a pharmaceutical to an animal comprising, a plurality of carriers comprising means for reversibly holding the pharmaceutical, a barrier comprising means for permitting passage of the pharmaceutical and for resisting passage of said carriers, said barrier being positionable within the animal such that said semipermeable barrier may define a first zone and a second zone within the animal, and a channel for passing into said first zone said carriers holding the pharmaceutical, whereby as the pharmaceutical is released from said carriers it may pass said barrier from said first zone into said second zone while said carriers remain in said first zone, wherein said channel comprises a conduit comprising means for traversing a body passage of the animal, and further comprising an injector for injecting said imbibed carriers through said conduit, whereby injecting said imbibed carriers effects the location of said barrier.

29. Apparatus for administering a pharmaceutical to an animal comprising, a plurality of carries comprising means for reversibly holding the pharmaceutical, a barrier comprising means for permitting passage of the pharmaceutical and for resisting passage of said carriers, said barrier being position within the animal such that said semipermeable barrier may define a first zone and a second zone within the animal, and a channel for passing into said first zone said carriers holding the pharmaceutical, whereby is the pharmaceutical is released from said carriers it may pass said barrier from said first zone into said second zone while said carriers remain in said first zone, wherein said channel comprises a conduit comprising means for traversing a body passage of the animal, wherein said conduit is provided with a retainer comprising means for resisting removal of said conduit from said passage.

30. Apparatus for administering a pharmaceutical to an animal comprising, a plurality of carriers comprising means for reversibly holding the pharmaceutical, a barrier comprising means for permitting passage of the pharmaceutical and for resisting passage of said carriers, said barrier being positionable within the animal such that said semipermeable barrier may define a first zone and a second zone within the animal, and a channel or passing into said first zone said carriers holding the pharmaceutical, whereby as the pharmaceutical is released from said carriers it may pass said barrier from said first zone into said second zone while said carriers remain in said first zone, wherein said channel comprises a conduit comprising means for traversing a body passage of the animal, wherein said conduit is provided with a retainer adapted to aid in preventing said conduit being drawn into the animal.

31. Apparatus for administering a pharmaceutical to an animal, comprising a porous semipermeable membrane that is a selectively permeable barrier having a porosity or mesh selected to permit passage of the pharmaceutical and to resist passage of carriers comprising means for storing and releasing the pharmaceutical, said barrier being positionable within the animal such that said barrier may define a first zone and a second zone within the animal, and a plurality of said carriers positionable within said first zone, said carriers comprising porous polymeric beads, whereby as the pharmaceutical is released from said carriers it may pass said barrier from said first zone into said second zone while said carriers remain in said first zone.

32. The apparatus of claim 31 wherein said porous polymeric beads comprise styrene divinylbenzene.

33. The apparatus of claim 31 wherein said porous polymeric beads are at least 5 microns in diameter.

34. The apparatus of claim 31 wherein said porous polymeric beads are at least 10 microns in diameter.

35. The apparatus of claim 31 wherein said porous polymeric beads include a network of pores in which the pharmaceutical can be reversibly held.

* * * * *